(12) United States Patent
Gershater et al.

(10) Patent No.: US 10,100,375 B2
(45) Date of Patent: Oct. 16, 2018

(54) MULTIFACTORIAL SCORING METHOD AND SYSTEM

(71) Applicant: SYNTHACE LIMITED, London (GB)

(72) Inventors: Markus Christian Gershater, London (GB); Sean Michael Ward, London (GB); Michael Ian Sadowski, London (GB); Christopher Richard Grant, London (GB)

(73) Assignee: SYNTHACE LIMITED, London (GB)

( * ) Notice: Subject to any disclaimer, the term of this patent is extended or adjusted under 35 U.S.C. 154(b) by 0 days.

(21) Appl. No.: 15/272,688

(22) Filed: Sep. 22, 2016

(65) Prior Publication Data

US 2017/0011045 A1  Jan. 12, 2017

Related U.S. Application Data

(63) Continuation of application No. PCT/US2015/022290, filed on Mar. 24, 2015.

(30) Foreign Application Priority Data

Mar. 24, 2014 (GB) .................................. 1405243.5

(51) Int. Cl.
*G06F 7/00* (2006.01)
*G06F 17/30* (2006.01)
(Continued)

(52) U.S. Cl.
CPC ........... *C12Q 3/00* (2013.01); *G06F 17/3053* (2013.01); *G06F 17/30528* (2013.01); *G06F 19/12* (2013.01); *G06F 19/70* (2013.01)

(58) Field of Classification Search
CPC . G06F 17/3053; G06F 17/30528; G06F 19/12
(Continued)

(56) References Cited

U.S. PATENT DOCUMENTS 6,931,396 B1    8/2005  Topaloglou et al.
8,180,615 B2 *  5/2012  Brown ................. B01J 19/0006
                                                                  703/11

(Continued)

FOREIGN PATENT DOCUMENTS

EP    2608122 A1    6/2013
WO    2010/098865 A1    9/2010

OTHER PUBLICATIONS

International Search Report and Written Opinion dated Jun. 29, 2015 in PCT/US2015/022290.
(Continued)

*Primary Examiner* — Binh V Ho
(74) *Attorney, Agent, or Firm* — Perkins Coie LLP; Alberto Araiza; Viola T. Kung

(57) ABSTRACT

Method, systems and apparatus to determine the suitability of parts or protocols to perform unit operations in the context of a biological process, comprising recording of a user score associated with an instance of use of a protocol or part, wherein the context of the use is recorded along with the rating, and wherein the context is defined as the value of factors that may affect the performance of the unit operation in which the part or protocol was used. The method may be implemented as a web service.

23 Claims, 4 Drawing Sheets

(51) Int. Cl.
*C12Q 3/00* (2006.01)
*G06F 19/00* (2018.01)
*G06F 19/12* (2011.01)

(58) Field of Classification Search
USPC .......................................................... 707/722
See application file for complete search history.

(56) References Cited

U.S. PATENT DOCUMENTS

| | | | | |
|---|---|---|---|---|
| 8,446,622 | B2* | 5/2013 | Han | G06F 3/1246 358/1.13 |
| 8,675,826 | B1* | 3/2014 | Bittner | H04M 3/493 379/72 |
| 8,756,050 | B1* | 6/2014 | Harkness | G06F 17/289 704/1 |
| 2002/0035506 | A1* | 3/2002 | Loya | G06Q 10/06 705/14.19 |
| 2004/0162852 | A1 | 8/2004 | Qu et al. | |
| 2005/0033568 | A1* | 2/2005 | Yu | G06F 17/276 704/10 |
| 2005/0149269 | A1* | 7/2005 | Thomas | G06F 19/28 702/19 |
| 2011/0131171 | A1* | 6/2011 | Jons | C12Q 1/6883 706/54 |
| 2012/0284257 | A1 | 11/2012 | Mousses et al. | |
| 2013/0144888 | A1* | 6/2013 | Faith | G06F 17/30696 707/748 |
| 2013/0205240 | A1* | 8/2013 | Ling | G06F 19/26 715/771 |
| 2014/0185954 | A1* | 7/2014 | Hsiao | G06Q 10/10 382/264 |
| 2014/0365278 | A1* | 12/2014 | Ashikawa | G06Q 10/06393 705/7.39 |
| 2016/0034514 | A1* | 2/2016 | Singhal | G06F 17/30867 707/706 |

OTHER PUBLICATIONS

Fu, Zhibiao et al., "Optimization of a Saccharomyces cerevisiae fermentation process for production of a therapeutic recombinant protein using a multivariate bayesian approach", Biotechnology Progress., vol. 28, No. 4, Jun. 18, 2012 (Jun. 18, 2012), pp. 1095-1105.

Orban, E., "Effect of temperature and yeast concentration on the autolysis of Kluyverommyces fragilis grown on lactose-based media", Journal of Food Engineering, vol. 21, No. 2, Jan. 1, 1994 (Jan. 1, 1994), pp. 245-261.

Saxena, Deepali et al., "Process optimization for a nutritious low-calorie high-fiber whey-based ready-to-serve watermelon beverage", Journal of Food Science and Technology, Springer (India) Private Ltd, India, vol. 52, No. 2, Jun. 25, 2013 (Jun. 25, 2013), pp. 960-96.

Supplementary European Search Report dated Jul. 17, 2017 in EP Application No. 15770388.5.

* cited by examiner

Figure 3

Part Assessment

Temperature: 20
Glycerol Content: 50
Incubation Speed: 1200

Potential Score: 5.0
Confidence: 1.0

MULTIFACTORIAL SCORING METHOD AND SYSTEM

This application is a continuation of PCT/US2015/022290, filed Mar. 24, 2015, which claims priority of GB 1405243.5, filed Mar. 24, 2014. The contents of the above-identified applications are incorporated herein by reference in their entirety.

FIELD OF THE INVENTION

Methods and systems for scoring elements of an experimental or production pipeline, in particular for bioprocess manufacturing or assays.

BACKGROUND OF THE INVENTION

When assembling a biological synthetic process, multiple alternatives typically exist for each of the operations and parts in the process, such as the structure and identity of the genetic constructs used, the particular protocol used to perform a step such as a transformation, purification etc. The question of how to design the most efficient process is therefore one of choosing a set of parts and operations, in order to satisfy design criteria such as maximising yield of the required output, etc.

There are very large numbers of variables that influence the overall yield of product in a biological synthetic process, such as the host organism selected and the particular strain of host species used, physical factors such as temperature, pH and oxygen availability and timing of reactions, to name a few. Therefore, the choice of suitable parts and operations that make up a multi-step process has to be made in the context of a highly dimensional design space.

Typically, these essential design decisions are made arbitrarily based on what is usual, available or known to the experimenter or manufacturer at the time of setting up the process or pipeline. Decisions in biological process design are often habitual or based upon artisanal know-how passed down within laboratories or industrial organisations. This is often complicated with time and resource constraints leading to a trial and error development in which a pipeline is adjusted by exchanging discrete parts and operations or modifying parameters, in order to improve the features of the starting pipeline. This results in design decisions that are often suboptimal or require substantial resources to identify reagents, operations and parameters that might be merely satisfactory. Hence, there can be considerable institutional resistance to change a process once it has been settled upon due to the inherent uncertainty associated with the optimization strategy as a whole.

There exists a need in the art, particularly within synthetic biology, to provide methods and systems that can facilitate the design of experimental or production pipelines from the level of the laboratory bench up to and including the industrial-scale bioreactor.

These and other uses, features and advantages of the invention should be apparent to those skilled in the art from the teachings provided herein.

SUMMARY OF THE INVENTION

In accordance with the present invention, a first aspect provides a method for scoring a unit operation comprised within a biological process undertaken by a user, the method comprising:

(a) a recording step in which the user records a score associated with an instance of use of the unit operation within a database, wherein the context of the use is recorded along with the score, and wherein the context is defined as the value of at least one factor that is deemed to affect the performance of the unit operation within the biological process; and (b) a retrieval step, in which the user specifies a proposed unit operation, and a proposed context for an intended use as a query within the database, and a score for relevant recorded unit operations is provided, wherein relevance of recorded scores is determined at least partially based on similarity between the context of the intended use and the context of the recorded use.

Typically, the score comprises one or more user-defined ratings and/or one or more measurable features associated with the use of the part or protocol.

In a specific embodiment the user is prompted to specify the value of specific factors during either the recording step or the retrieval step.

In a further embodiment of the invention, the user may specify criteria on scores to be included or excluded. Suitably, recorded scores within a user-defined distance from the proposed context or within a user-specified area of the context space may be returned. In a specific embodiment, the retrieval phase returns a set maximum number of alternative parts or protocols.

In yet a further embodiment of the invention, a score is associated with a confidence metric. Suitably, the confidence may be defined in relation to the user who defined the score. In a particular embodiment, the confidence is calculated based on how many scores were submitted by a user, and how often a user's scores agree with other users. Optionally, the confidence may be defined in relation to the similarity between the proposed context and the context of recorded scores. In a specific embodiment of the invention, the confidence is defined in relation to the amount of contextual information provided with the score.

In a specific embodiment, similarity is defined using a distance metric, suitably Euclidian distance.

In a further embodiment of the invention, cut-offs for scores to be considered are dynamically defined based on a statistical metric of reliability.

In yet a further embodiment, the context of a part, protocol or unit operation comprises features of preceding or subsequent unit operations. Optionally, incompatible options may be automatically filtered.

In a specific embodiment of the invention, the user may prioritise features of interest in the evaluation of the similarity between contexts. Suitably, the user may specify weights or rank the features of contexts to be compared.

In a particular embodiment of the invention, multivariate models may be fitted to describe the scoring space.

A second aspect of the invention provides a system for scoring parts and protocols in a biological process, the system comprising:

(i) a server with processing modules adapted to implement the method comprising any of claims 1 to 21;
(ii) a data storing means for recording the scores, context and user information, which is accessed by the processor;
(iii) an interface for accessing the method.

Typically, the data storing means is a data base or the data is provided through a cloud service. Suitably, the system comprises a website or a mobile device or computer application to access the service. Optionally, the system may be incorporated as part of a laboratory information management system.

A third aspect of the invention provides a method for performing a biological process, the method comprising:
(a) defining at least one query unit operation required to complete the biological process, wherein the query unit operation comprises a protocol that requires the use of least one part in order to complete the protocol;
(b) providing a database, wherein the database comprises a plurality of rated unit operations, wherein each of the plurality of rated unit operations comprises a multidimensional rating associated with it;
(c) searching the database with the query unit operation in order to identify one or more compatible rated unit operations, wherein the most compatible rated unit operation is selected on the basis of the distance between the multidimensional rating of each rated unit operation and the at least one query unit operation;
(d) performing the biological process using the most compatible rated unit operation identified for the process.

Typically, at least two unit operations are required to complete the process. Optionally, a plurality of unit operations are required to complete the process.

Optionally, the method may comprise an additional step of:
(e) following completion of the most compatible rated unit operation submitting a score to the database, wherein the score comprises at least one user-defined rating relating to the performance of the most compatible rated unit operation within the biological process.

Suitably, the score may further comprise at least one feature associated with a part or with a protocol used in the performance of the most compatible rated unit operation within the biological process.

A fourth aspect of the invention provides a computer readable medium comprising a database, and the database comprises a plurality of unit operations, each unit operation being suitable for use within a biological process and wherein each unit operation is defined as a protocol that requires the use of at least one part in order to complete the protocol, and wherein each unit operation is associated with a multidimensional score.

In a specific embodiment of the invention, the multidimensional score comprises at least one user-defined rating. Suitably, the multidimensional score further comprises at least one item of contextual information, wherein the at least one item of contextual information comprises the value of at least one factor that is deemed to affect the performance of the unit operation within the biological process.

A fifth aspect of the invention provides an apparatus comprising the aforementioned computer readable medium described herein.

In a specific embodiment, the apparatus comprises one or more memories and one or more processors, and the one or more memories and the one or more processors are in electronic communication with each other, the one or more memories tangibly encoding a set of instructions for implementing the aforementioned methods described herein.

BRIEF DESCRIPTION OF THE DRAWINGS

FIG. 3 is a score presentation window according to one embodiment of the invention.

DETAILED DESCRIPTION OF THE INVENTION

Figure 1:
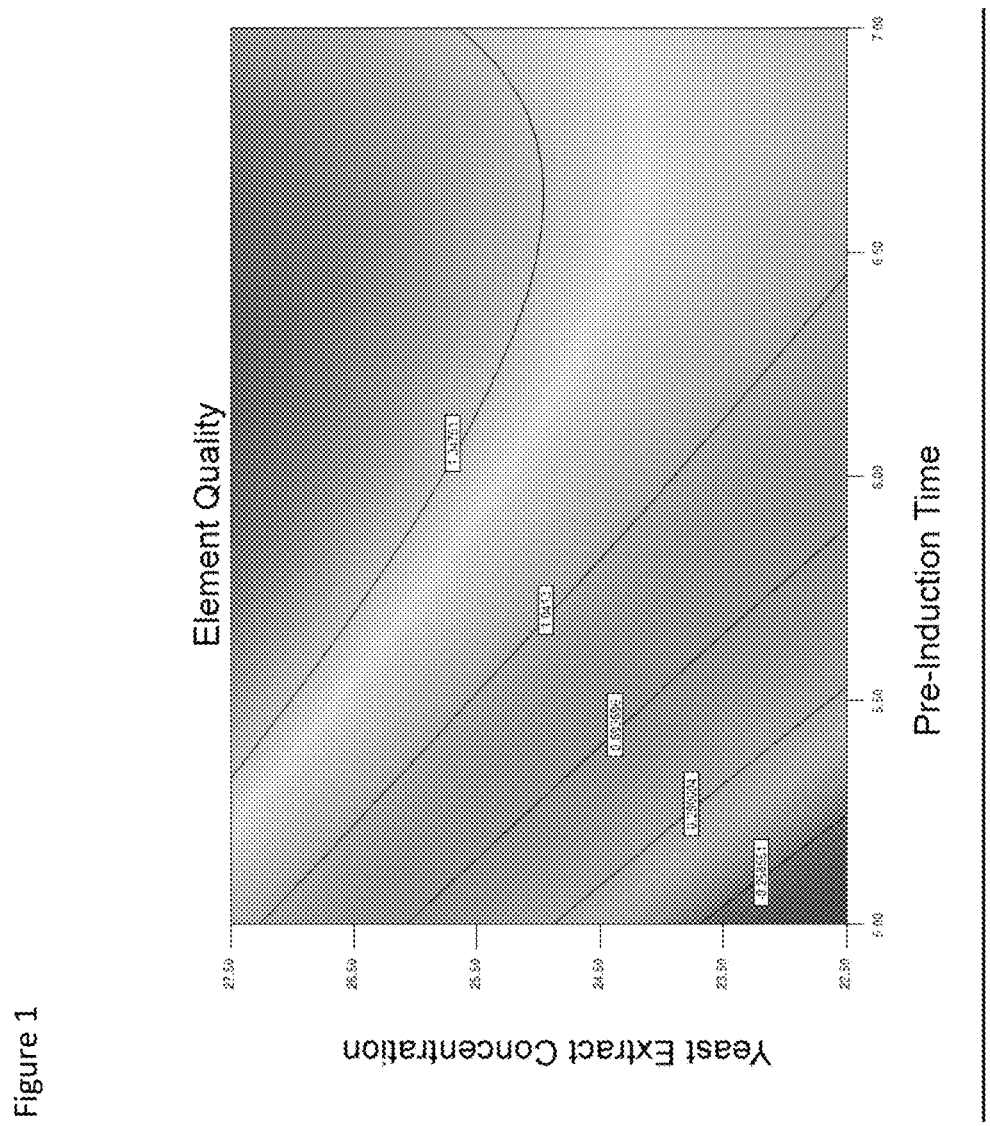
FIG. 1 is a fitness landscape for a part or protocol according to one embodiment of the invention.

All references cited herein are incorporated by reference in their entirety. Unless otherwise defined, all technical and scientific terms used herein have the same meaning as commonly understood by one of ordinary skill in the art to which this invention belongs.

Prior to setting forth the invention, a number of definitions are provided that will assist in the understanding of the invention.

As used herein, the term "comprising" means any of the recited elements are necessarily included and other elements may optionally be included as well. "Consisting essentially of" means any recited elements are necessarily included, elements that would materially affect the basic and novel characteristics of the listed elements are excluded, and other elements may optionally be included. "Consisting of" means that all elements other than those listed are excluded. Embodiments defined by each of these terms are within the scope of this invention.

The term "process" is defined as a specific sequence of transformative events, comprising unit operations, performed upon a starting material in order to achieve a specified technical purpose or goal. The process may result in the transformation of the starting material into a product—in which case the process is a "production process". Alternatively, the process may result in the determination of information about the starting material—in which case the process may be diagnostic or prognostic in nature. The overall process may be subdivided into individual process steps that are applied in sequence to achieve the desired outcome. According to an embodiment of the invention, the process is a "bio-process" that uses complete living cells or their components (e.g., prokaryotic or eukaryotic cells, enzymes, or organelles such as chloroplasts) to obtain desired products.

The processes of the present invention comprise steps or unit operations that are applied on or require parts. Hence, in accordance with the invention a process comprises a set of steps—unit operations—that are applied on inputs (including at least a physical input)—parts—in order to produce an output (including at least a physical output such as a product, and possibly additional data outputs). An embodiment of the invention may include a process which involves the introduction of one or more genes into a microorganism, which in turn expresses one or more proteins encoded by those genes. The protein(s) itself is may be the desired product or where it functions as part of a pathway, the protein may contribute to the generation of a desired product.

The term "unit operation" is defined as any step or sub-step in a process that can be identified as a self-contained process or "unit" which contributes to a set of successive steps—or units—that together serve to make up a complete process. Suitably, a unit operation may be selected from one or more of: a conversion; a reaction; a purification; a construct assembly step; an assay or analysis such as a quantification of a product, a by-product or reagent; a sequencing of nucleic acids; a physical mixing; a centrifugation; a spreading or physical plating of a sample; the selective sampling of a sub population of a sample, such as colony picking; the three dimensional placement of a sample into a structural matrix; a nucleotide or protein/peptide synthesis; a fermentation; a cell culture; an incubation; a restriction; a ligation; a mutation; a transformation; a specific computation analysis, such as a linear regression, sequence alignment, or model based prediction; a separation such as chromatography; a filtration; a concentration; an evaporation; a desiccation; a wash; an extraction; the conditioning of a product (e.g. for storage); and an amplification (e.g. with respect to a nucleic acid). It will be appreciated that the aforementioned does not represent an exhaustive list of potential unit operations, which are typically reliant upon the precise nature of the process that is to be undertaken.

The term "parts" refers to any physical element utilised within a process or unit operation. Suitably, a part may be a reagent, product, or input to any unit operation, or any piece of equipment or apparatus that is used in a process or unit operation. Typical parts may be selected from one or more of: a variant of a gene or polynucleotide; a genetic construct; a whole cell or cell line; an enzyme; an antibody; a small molecule; a solution (such as buffers, reagents, culture media, etc.); a solid support; a container (such as reaction tanks, flasks, slides, beads or physical interaction substrates, etc.); a peptide; a polypeptide; a functional or non-functional nucleic acid; a nutrient compound; a growth factor; a cytokine; an element; an ionic substance, such as an organic or inorganic anion or cation; and a gas or vapour in the environment of the process. It will be appreciated that the aforementioned does not represent an exhaustive list of potential parts, which are typically reliant upon the precise nature of the process that is to be undertaken.

The term "product" is defined as any desirable physical output of a process. Suitably, a product may include an eukaryotic or prokaryotic organism, virus, nanostructure, a protein, polypeptide, polynucleotide, polymer, tissue, complex or small molecule that is produced as a result of the process. In some processes the product is in fact an information object, such as a digital genetic sequence, or a measurement of system properties that is the result of a destructive or non-destructive assay. It will be appreciated that the aforementioned does not represent an exhaustive list of potential products, which are typically reliant upon the precise nature of the process that is to be undertaken.

The term "protocol" refers to a set of instructions for performing a unit operation. Typically, the set of instructions may be a non-exhaustive list of actions and associated parameters that have to be performed, such that a series of variables are set by the protocol while additional variables are left to the user. Typical variables that are set by a protocol may include the identity and/or concentration of inputs to the operation, the order and/or timing of performing various steps in the protocol, the value of physical parameters which have to be set for some or all steps of the protocol (such as e.g. the temperature, pH, oxygen concentration, mixing speed, etc.), features of the equipment used, and factors such as selecting between alternative calculation models or analysis techniques for computationally derived steps. It will be appreciated that the aforementioned does not represent an exhaustive list of potential elements of a protocol, which are typically reliant upon the precise nature of the process that is to be undertaken.

The processes of the present invention are subject to process variables that are referred to as factors. The term "factor" is used herein to denote any defined feature of or within a process or protocol that can be modified without changing the ultimate goal of the process. Collectively, these factors constitute the "context" of a process. According to one embodiment of the present invention there are two categories of factors: genetic and process factors.

"Process factors" suitably relate to features of a process which are not associated with the genetics of a construct or host. Typical process factors may include features of the equipment (e.g. dimensions of a reaction tank, impeller configurations, siting of probes), environment (e.g. temperature, pH, oxygenation, atmospheric pressure), protocol (e.g. timings of significant stages and events such as inoculation and induction), reagents (growth media composition, nutrient level, feedstock concentration, inducer concentration), handling of cells (stock storage conditions, size of inoculations between reactors), process design (number of process steps, type of reaction vessel). It will be appreciated that the aforementioned does not represent an exhaustive list of potential process factors, which are typically reliant upon the precise nature of the process that is to be undertaken.

"Genetic factors" suitably relate to qualitative and quantitative features associated with any genetic material involved in a process, for example, such as features of the specific genetic 'construct' which is used to introduce new nucleic acid, including DNA, into the host (e.g. identity or composition of vector), features of the host microorganism (e.g. strain, genetic background (including knockouts of undesirable genes and protein overexpression, epigenetic factors), features of functional DNA (e.g. promoter strength, ribosome binding site strength, plasmid origin of replication, terminator, codon usage strategy, operator, activator, gene variant). It will be appreciated that the aforementioned does not represent an exhaustive list of potential genetic factors, which are typically reliant upon the precise nature of the process that is to be undertaken.

The term "score" refers to any interpretable objective or subjective measurement of the suitability of a part, unit operation or protocol for a given purpose within a process. Suitably, a score may be in the form of a user-defined rating (such as e.g. in a range of a minimum to a maximum number of stars, points, or a Boolean thumbs up or thumbs down.), a grade, a proportion of positive evaluations, or a colour (such as a traffic light ranking). In some embodiments, a score may be in the form of a quantifiable or measurable feature of a part or operation, such as e.g. the quantity, purity, productivity, efficacy of a product output; the quantity of a by-product or contaminant present; the yield of a process; and the cost, energy or time efficiency of a part or unit operation. It will be appreciated that the aforementioned does not represent an exhaustive list of potential scores, which are typically reliant upon the precise nature of the process that is to be undertaken.

The term "context" as used herein refers to the situational information associated with a specified user. Context as applied to a multidimensional rating or score provides a perspective to the value ascribed by a score. It will be appreciated that virtually every user will have a unique perspective when providing a rating for any a given unit operation. The context will depend, in part, upon the parts available to the user, the success of those parts (e.g. apparatus, infrastructure) in performing a unit operation, the success of the unit operation within the process as a whole or in combination with other unit operations (e.g. compatibility with other unit operations) and any factor variables associated with the user.

In a specific embodiment of the invention, a score comprises a multidimensional rating obtained from a combination of one or more user-defined assessment measures and/or one or more measurable features of a part associated with an instance of use of a particular part, protocol or unit operation. Suitably, a score may be obtained from one or more user-defined ratings of one or several aspects of a part or protocol (such as e.g. yield, ease of implementation, cost, etc.)—in this instance the score will comprise a level of subjectivity. Alternatively, a score may be obtained from one or more measured features of a part or protocol, such as the stated output yield, quality control measurements, and successful completion of control experiments. In such an instance, the score will comprise a greater level of objectivity. The presence of one or more measured factors may also contribute towards the determination of a multidimensional rating that ultimately results in a score. Typically, in a specific embodiment of the invention the score is derived from a combination of one or more user-defined ratings and one or more measured features. A score can suitably be obtained from one or more users and/or one or more instances of use of a part, protocol and/or unit operation.

The values of factor variables in a process (i.e. the context of the process) typically contribute to determining the performance of a particular protocol or part. In other words, the suitability of any given alternative is not necessarily inherent to the protocol or part but may depend on the context of its intended use. By way of example, in a particular unit operation the user's choice of which host organism to use (i.e. a choice of "part") may affect the type of reactor vessel available (i.e. the choice of another "part") and the culture conditions required (i.e. the choice of a "protocol"). It therefore becomes critical to characterize what regions of the design space a particular part of protocol will operate reliably within the unit operation.

Traditional models for attributing a rating to an object have relied upon the ability to assign an absolute score, or at the minimum a distribution of scores that is representative of the inherent worth of an object. Such examples of said scoring systems include the ratings of apps on mobile phone marketplaces, of books on web portals, of accommodation on hotel booking websites, or of music or movies in video or music streaming/retail services. A common metric is to rate something as between one to five stars, with the mean average of all users who have scored an item being displayed as the conclusive "rating" of the object.

Additional innovation in the space has included tracking versions of an object, such as a software application, with aggregated ratings by version (such as allowing the scores of an application to be compared between the current version and past versions, as things may have changed), and to allow the viewing of the distribution of scores, such as how many one star versus five star ratings have been collected. The latter is very important in the scoring of highly subjective objects, such as music or movies, which may not have a true absolute score to be determined. Scoring systems for objects with context dependent value has been overlooked. The present invention provides an improved method in order to determine the suitability of parts or protocols to perform unit operations in the context of a biological process.

According to one aspect, the invention provides a novel methodology that involves the combination of a collection of parts and protocols associated with a unit operation, with user ratings to score said parts and protocols with regard to the user's specified context.

A specific embodiment of the invention provides a computer implemented database comprising a plurality of parts and/or protocols which can contribute to unit operations within an experiment or process. In one embodiment of the invention, the database comprises a plurality of parts and associated protocols that may use those parts. Optionally, the database may be hosted on a server that is accessible remotely, such as via internet or intranet connection. Users are able to access the database and select unit operations in order to complete a desired process or experimental pipeline. The selection process may be completely open and subject to the user's own selection criteria, or alternatively the selection process maybe fully or partially guided with reference to the user's individual context. After the user has completed at least part of a protocol—typically once they have completed a unit operation—the user is prompted to rate the parts and/or the protocol used and the value of any associated factors may be recorded along with the rating. The user's rating may be combined with further additional information that is context specific. Hence, each such rating submitted by a user defines a point in a multidimensional space, where the dimensions represent multifactorial parameters of the process. The ratings in multidimensional space form a fitness landscape, allowing new experiments or parts to be compared for similarity to known ratings. It can be appreciated, therefore, that the present invention provides a method for providing context specific rating for unit operations within a given process or experiment. Hence, when choosing unit operations for other processes, users are able to select rated parts, protocols and unit operations from within the database that are most appropriate to the context of the user.

Figure 2:
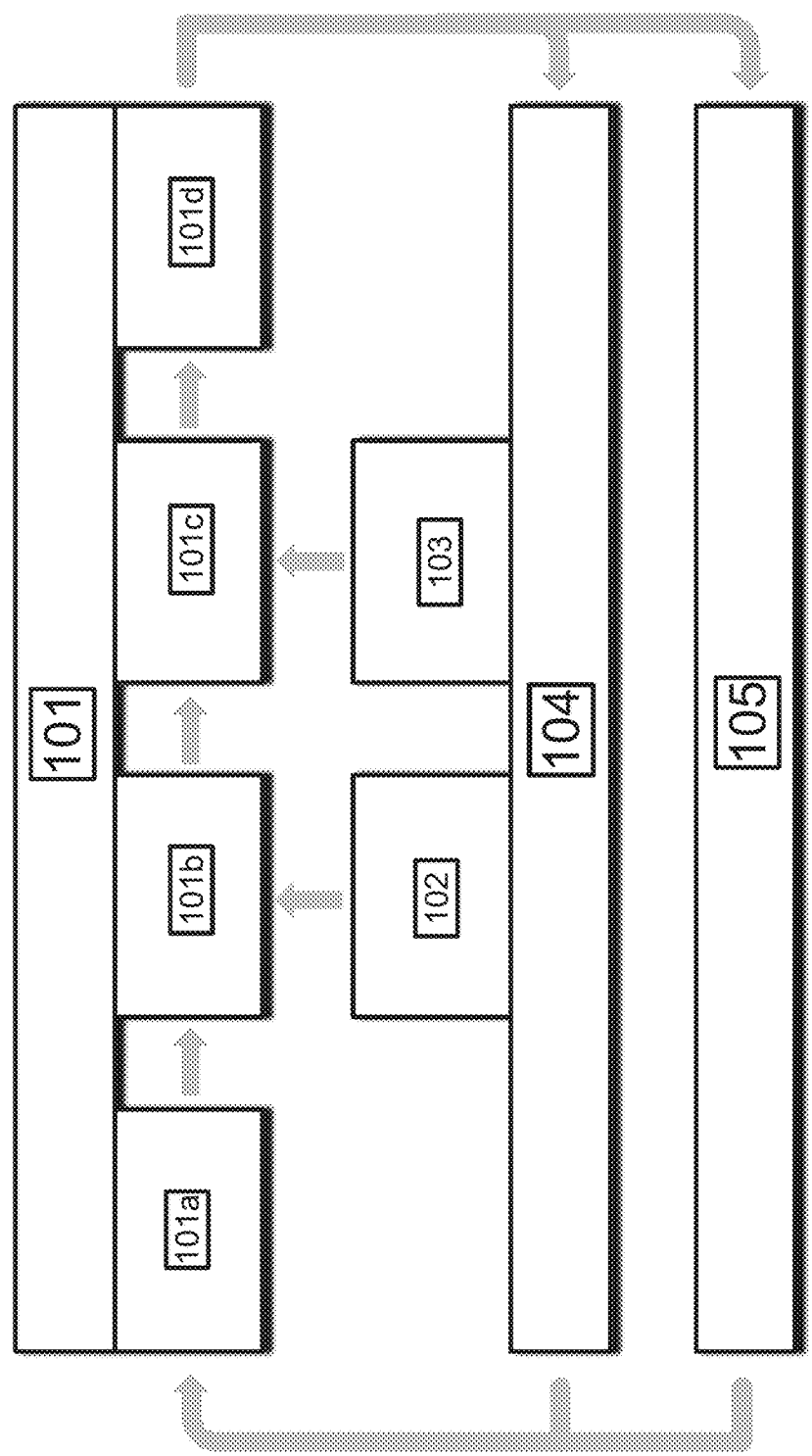
FIG. 2 is a flow diagram of a computer implemented platform for the design of experiments or biological processes by a user that utilises various interacting modules according to one embodiment of the invention.

FIG. 2 is a flow diagram that shows a computer implemented platform for the design of experiments or biological processes by a user that utilises various interacting modules. In one embodiment of the invention the user will access the platform via a user interface (105) so as to access a workflow design tool (101). The user interface (105) may be comprised within a laboratory information management system (LIMS) package, via a dedicated software application (an 'app'), via a website or any other suitable user interface. The workflow design tool (101) enables the user to specify the type of experiment or biological process that is under consideration, especially by specifying inputs (e.g. starting materials) and the desired outputs (e.g. products). In defining the objectives of the experiment or process the workflow design tool (101) the user is able to access the experimental design module (101a) which provides a mechanism for breaking down the experiment or process into one or more unit operations.

Each unit operation will comprise one or more parts and one or more protocols. Selection of the most appropriate components of the one or more unit operation can be accomplished within the parts module (101b) and the protocols module (101c). The parts module (101b) and the protocols module (101c) respectively are able to access a library of compatible standardised parts and protocols comprised within a parts characterisation module (102) and a protocol definition module (103). A fully assembled workflow provides a process pipeline that comprises at least one unit operation, more typically a plurality of unit operations such as the one shown in FIG. 2. The fully assembled workflow can be tested for compatibility with the user's available parts—including laboratory automation apparatus—so as to provide a validation of the workflow within the specific context of the user. Validation can be carried out via the analysis module (101d). It is optional for unit operations to subject to associated scoring or rating criteria that allow for comparison of the user's unique context with the suggested workflow. Hence, the workflow design tool (101) provides capability to establish a design space in part defined by the user's unique context and, in so doing, only permits assembly of a workflow that is compatible with the user contextualised design space.

One important aspect of the platform is that it permits certain degrees of freedom for users to modify unit operations in order to improve compatibility with available parts and associated protocols. This advantageously enables a level of flexibility within the design space as well as an evolution of unit operations to accommodate slightly different user contexts. Once a validated process pipeline is approved by the user the workflow can be implemented either via fully automated laboratory systems or via a manual implementation, or a combination of both. As the unit operations within the pipeline are completed the laboratory automation apparatus and/or the user are prompted to provide feedback metrics on the successful performance of the unit operation as well as the assembled pipeline as a whole. In an embodiment of the invention the feedback metrics include, scores and ratings, as well as factors such as data and information on reaction conditions, yield of product, time taken for completion of the protocol, purity of the product, amongst others. The feedback metrics may be combined together with the information regarding the process pipeline and communicated to a standardisation engine (104).

The standardisation engine (104) provides a function of data standardisation, including normalisation, reformatting and parsing on the input information that includes the pipeline process assembly and any accompanying modifications made by the user, together with associated metrics and scores. Data standardisation may comprise removal of extraneous or irrelevant information as well as normalisation of data or values to common or standard form, such as via reference to lookup tables. In so doing, the standardisation engine (104) transforms the input data into a common representation of values thereby providing a consistent record. The standardisation engine (104) may comprise a database of standardised unit operations, parts and protocols, optionally with associated multidimensional scores. Optionally the standardisation engine (104) does not comprise a database itself but communicates with a database within a separate module (not shown), or within one or more databases comprised within the workflow design tool (101). The standardisation engine provides standardised descriptions of parts to the parts characterisation module (102) and the protocol definition module (103) respectively. Hence, the computer implemented platform provides an iterative procedure for assembling unit operations from standardised parts and procedures that are continually improved, adapted and modified dependent upon the user's context. Where the platform is accessed by multiple users, such as in the instance of a multi-user cloud or internet based platform, users will benefit from the continual generation of novel and/or improved parts, protocols and associated unit operations.

According to an embodiment of the invention, a user may fully or partially specify the parameter space of a proposed unit operation. This may then be used to search for any scorings of potential parts and/or protocols (for a given purpose) that exist within a region of the parameter space around the proposed unit operation. This allows a subset of the available scores to be extracted to provide a context-dependent score to the parts or protocols in the database that fulfil the given purpose.

In an embodiment of the invention, the method may automatically identify whether any information is lacking for a rating to be informative—i.e. whether the proposed rating does not comprise sufficient information to establish a meaningful point in a multidimensional space, wherein the dimensions represent multifactorial parameters of the process. This validation procedure can be performed at the rating recordal step, whereby a user is prompted to provide a value for relevant factors associated with an instance of use of a part or protocol upon recordal of the rating of the object. Alternatively, this can be undertaken at the score retrieval step, whereby a user is prompted to provide the value of relevant factors of the proposed unit operation before retrieval of relevant scores from the database. Suitably, this can be done both at the recordal and retrieval step. All or most aspects of the rating process may also be automated, as described in further detail below.

In certain embodiments of the invention, multidimensional ratings comprise a combination of quantitative and qualitative values. Optionally, multidimensional ratings comprise only qualitative values, such as Boolean thumbs up vs thumbs down scorings. Suitably, all rating dimensions may be quantitative values. When all dimensions are quantitative values, a distance metric, such as Euclidian distance, Manhattan distance, or any other distance metric known in the art, may be used to compare rating records. Suitably, qualitative scores may be assigned equivalent numerical values (for example a "thumbs up" rating may be given a score of 1, with score 0 assigned to a "thumbs down") and techniques applicable to quantitative data applied.

In a further embodiment, the method includes tools to specify which dimensions are to be prioritised when comparing rating records by a user. Suitably, a weight table may be supplied by a user upon score retrieval. Preferably, dimensions are quantitative and a weighted distance measure may be calculated. In alternative embodiments, a user may specify a ranking of dimensions. In some embodiments, a user may optionally exclude particular dimensions.

According to one embodiment of the invention, one or more criteria may be applied to the distance between recorded instances and the potential unit operation specified by the user in order to retrieve the most relevant scores. Suitably, a cut-off on the distance may be specified by the user. In alternative embodiments, a cut-off on the number of different points may be specified by the user, where a point corresponds to a particular context, and multiple instances with individual ratings may map to a given context. Suitably, a region of the multidimensional space may be specified by the user for extraction of relevant scores. In some embodiments, a user may specify criteria on those scores that should be included or excluded from consideration. Suitably, a user may specify that only high confidence scores are to be extracted. Hence, confidence of a score may be defined in relation to the user who defined the score. Optionally, confidence of a score may be defined in relation to a measure of replicability of the rating. In some embodiments, cut-offs for scores to be considered may be dynamically defined based on measures of local variance, noise metrics, or any other statistical metric of reliability of a quantitative variable.

In a specific embodiment of the invention, the distance between the proposed experiment space and the existing score records for the selected unit operation(s) may be used to return a confidence score. Suitably, this score may be displayed to the user along with the scores provided for the unit operation(s) themselves.

In some embodiments, compatibility ranges for some or all parameters may be taken into account to filter out incompatible options. Compatibility of chosen options may be checked along an entire pipeline, i.e. a succession of unit operations and associated parts. Suitably, the context of a score includes information about the preceding steps in the pipeline. The context of a score may include information about the subsequent steps in the pipeline. In some embodiments, the context of a score includes information about parts used in subsequent of preceding steps in the pipeline.

An additional optional feature allows the provenance of the user who provided a score for a part or protocol to further weight the returned scores, allowing the scores of high quality users to be ascribed more weight in the assessment of the context dependent scoring of a part of protocol. Such provenance or "trustworthiness" rating may be a function of the number of scores submitted by a given user, either in total or over a specified timer period. Suitably, this trustworthiness rating may be obtained automatically by scoring how often the user's scores agree with other user scores. Typically, only those user scores that fall within a specified cut-off distance of the assessed user are made available for comparison.

In an embodiment of the invention, multivariate models may be fitted to describe the scoring space. Suitably, multivariate models may be fitted when sufficient scorings have been collected to fit a model within a reasonable noise threshold. This embodiment of the invention is especially beneficial when the scoring metric represents an objective 'real world' measure, such as enzyme activity or temperature, as it allows more robust models to be generated directly from sufficient numbers of user generated experimental scores. These multifactorial models can in turn improve the quality of predictions for compatible objects. The prediction interval, or a finer grained prediction variance surface may be computed as well, to provide a direct measure of the prediction confidence score in concert with a rating.

In specific embodiment of the invention, a user may select a part, protocol or unit operation and directly access information about the part or protocol. In some embodiments of the invention, a user may be presented with options to purchase a selected part or protocol. Hence, the invention may provide additional functionality that includes a link to one or more online vendors who are able to supply the specified part, protocol or unit operation. The retail functionality may be hosted within a cloud-based server. Optionally, the retail functionality may be comprised within an online marketplace that may be integrated within or an adjunct to a computer implemented system of the present invention.

In a specific embodiment of the invention, the described method can be implemented via one or more computer systems. According to a further embodiment, an apparatus comprising one or more memories and one or more processors is provided, wherein the one or more memories and the one or more processors are in electronic communication with each other, the one or more memories tangibly encoding a set of instructions for implementing the described methods of the invention. In another embodiment the invention provides a computer readable medium containing program instructions for implementing the method of the invention, wherein execution of the program instructions by one or more processors of a computer system causes the one or more processors to carry out the steps as described herein. Suitably, the data may be stored in a database, and accessed via a server. Suitably, the server is provided with communication modules to receive and send information, and processing modules to carry out the steps described herein. In some embodiments, the data is provided through a cloud service. In preferred embodiments, the method is accessible as a web service. In some embodiments, users may access the service for recordal or retrieval of scores via a website, in a browser. In some embodiments, an application for computes, tablets or smartphones may be provided to access the service. In some embodiments of this invention, the method may be incorporated as part of a laboratory information management system.

The invention as described provides, in one embodiment, a design method for a laboratory/manufacturing bio-process in which a user can select the most appropriate unit operations in order to create a bio-process that is most appropriately configured to the user's needs and available resources—i.e. the user's starting context. Such resources may include the available equipment, starting materials, time and/or cost. In order to provide the most appropriate bio-process that is contextualised to the needs of the user, each unit operation within the process is scored appropriately and the user is able to select those which are most appropriate to their needs. In this regard, the user's specific context can be determined within the process of the invention, such that the user's requirements determine a design space which in turn defines unit operations available to them.

In a particular non-limiting illustration of the invention in use, a user may require a protocol for expression of a modified enzyme product from a particular microbial host organism. Such a protocol will be comprised of a plurality of unit operations that may include: (i) a gene assembly step to generate the gene encoding the modified enzyme; (ii) a vector insertion step to insert the modified gene into an appropriate expression vector; (iii) a microbial host transformation step; (iv) a selection step to identify and isolate host clones successfully transformed with the vector; (v) a growth step to expand transformed host cells; (vi) product expression steps; (vii) one or more product isolation and purification steps; and (viii) one or more validation steps to determine adequate quality control of product. As is evident from this exemplary protocol, there are a great many design choices available to the user not just at every individual unit operation but in relation to combinations of unit operations. Multiple factors will affect the performance of each unit operation as well as the interactions of adjacent unit operations. By way of example, the selection of microbial host organism (e.g. prokaryotic versus eukaryotic) will determine which vectors are suitable for transformation, as well as the various process steps necessary to ensure efficient production of the desired enzyme product. However, even with such constraints on the system the plurality of available protocols that exist in the prior art for each unit operation is such that even the most standard bioprocess can result in a near infinite number of combinations of unit operations, thereby determining an insurmountable multi-dimensional design space for the user. According to an embodiment of the present invention, the complexity in this design methodology is reduced by providing contextualised scoring of each unit operation required for completion of the process such that a best-fit combination of unit operations can be assembled that reflects the user's own needs, available apparatus and resource constraints (i.e. within the specified design space). The assembly of a process from the unit operations that have the highest rating score permits the process to be optimised to the particular context of the user, thereby facilitating greater efficiency, predictability of outcome, reproducibility and yield. The selection of potential candidate pathways may then be transformed into a graph max-flow connectivity problem, where nodes represent the process element options, and the edges represent the compatibility of the two process elements in the current proposed experiment space. Many existing algorithms, including clinic's algorithm, MPM algorithm, and binary blocking flow algorithm can be used to then find optimal compatible elements for the experimental space. It will be appreciated that the aforementioned algorithms are not an exhaustive list of max flow calculation.

Figure 4:
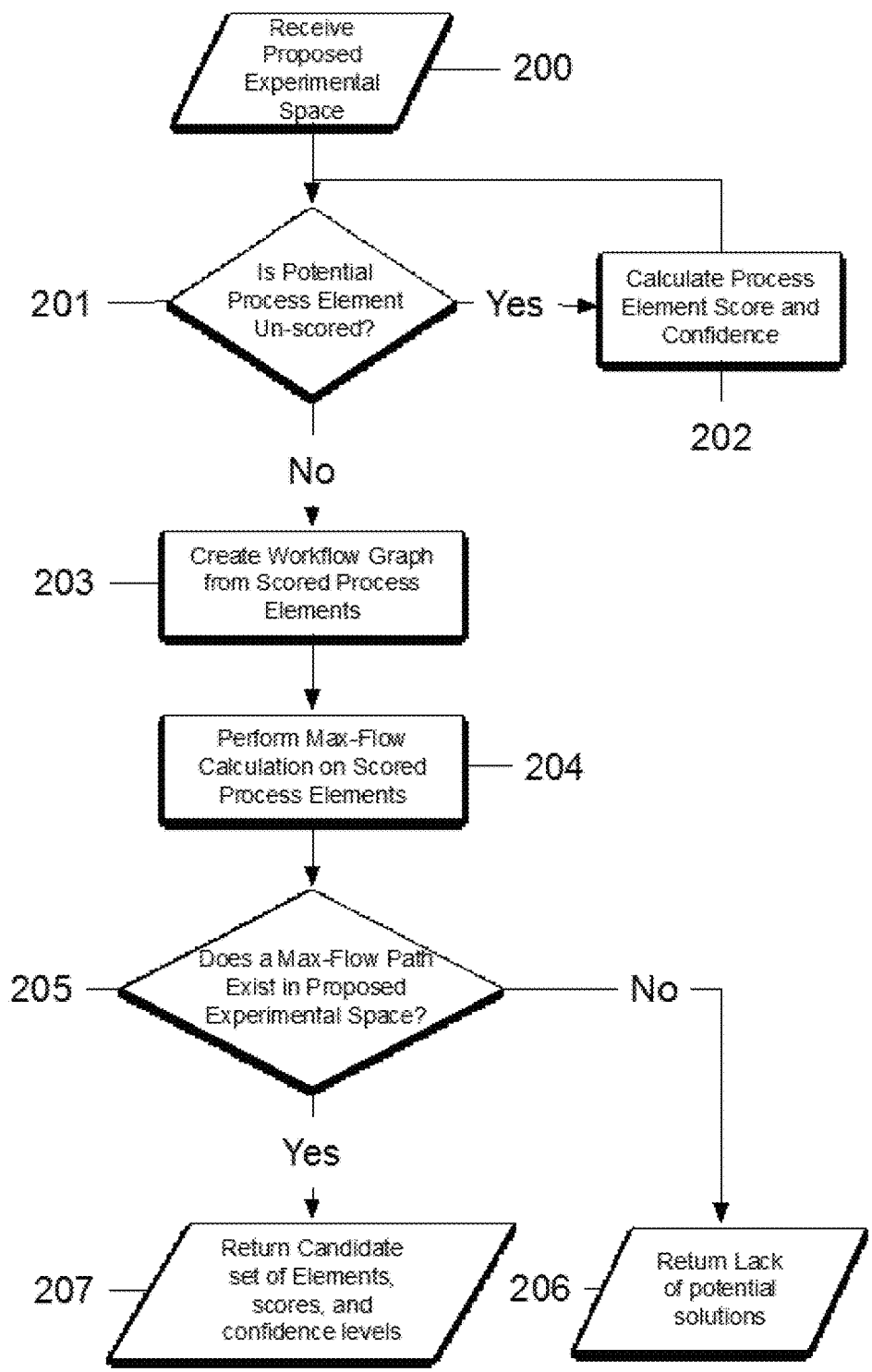
FIG. 4 is a flow diagram of a process design according to one embodiment of the invention.

FIG. 4 is a flow diagram that shows a process design for a process including multiple unit operations, according to an embodiment of the invention. At step 200, a user may specify a proposed experimental space in which the process will be performed. At step 202, the score and confidence associate with elements in the process may be calculated if not already available (step 201). The scored process elements may then be used to create a workflow graph at step 203. The workflow graph may then be used at step 204 to find a max-flow path. If a max flow path cannot be found, the user may be informed at step 206 that potential solutions were not found. If a max-flow path was found (step 205), the candidate set of elements, associated scores and confidence levels may be returned at step 207.

It will be appreciated that according to embodiments of the invention the entire user interaction process is iterative, such that the greater the level of user interaction the more rating information is captured. Consequently, the ability to define unit operations multi-dimensionally also improves.

The invention is further illustrated by the following non-limiting examples.

EXAMPLE

Example 1

Scoring of a Protocol

FIG. 1 shows an example of a three-dimensional situation in which an element quality score (either subjective or objective) is modelled as a function of two input variables: Yeast Extract Concentration and Pre-Induction time. The scenario from which this arises is an element encoding a process for expression of a protein from a genetically modified host in which the protein expression is under control of an inducible promoter system. The element has two input parameters: the time before protein expression is induced (pre-induction time) and the concentration of a nutrient-bearing media component (yeast extract concentration). In the example shown the element has been characterised using a multifactorial response surface experiment in which 11 runs have been performed across five input values of the two parameters. The colour in the figure then represents the 'height' of the modelled fitness landscape which has been derived from the experiments using an objective measure which represents the amount of target protein produced for given values of the inputs.

The model fit in question is a linear model containing first and second-order terms in the two inputs along with an interaction term and a single normally-distributed error term. This defines one aspect of the quality of the element in a multivariate context when measured solely as a function of the functional protein yield expected and shows that in this case the yield is minimal for the lowest tested values of both inputs and maximal for high yeast extract concentration and intermediate pre-induction time.

This process could be exactly replicated for any alternative quality metric such as another objective measure (biomass yield, efficiency of conversion or any other such measure) or subjective user ratings given for each of the eleven experiments. The modelled surface represents a prediction for all values of inputs based on a fit to the eleven measurements taken—since all such predictions are subject to prediction error it is important to provide estimates of confidence around the expected quality value predicted for any combination of input variables.

The degree of prediction error depends on the structure of the experiments used and the error variance of the system. In the example the prediction variance is approximately constant for a region circumscribed by a circle passing through the most extreme experimental design points, and increases rapidly outside this circle. Predicted quality values can be produced with confidence intervals using this model regardless of where the actual experimental points are situated, leading to a method for dealing with missing data: how to estimate the quality in untested situations. Alternative experimental designs including ad hoc approaches will lead to different prediction error surfaces and in most cases more variable levels of prediction error between different parts of the space.

Where factors are discrete values rather than continuous this approach is less suitable and it may be necessary to use a nearest-neighbour approach. In this method the quality would be defined for certain combinations of categorical input variables and the value for a new combination of input variable values (of which all values have been individually tested at least once) may be estimated by either the direct inheritance of the value for the most similar measurement in the dataset (in which multivariate similarity is defined using one of a number of applicable distance measures such as Euclidean distance, Manhattan distance or any formal or informal metric) or by averaging over values weighted by a distance measure. Prediction error in this instance may be modelled using a function of the applied distance parameterised by cross-validation.

In the example shown the values of the parameters corresponding to changes in the values of input variables embody a notion of relevance of differences in each dimension as contributors to element quality in those circumstances. Large model coefficients imply high relevance of changes in the variable in question to eventual quality while smaller values imply low relevance. In addition to this fixed-effects model a layer of random-effects terms may also be added which model the degree to which variability of quality output is dependent on changes to the input. This adds an additional definition of relevance: a factor may be highly relevant to quality of element performance either by contributing to the mean or the variance of a measured output.

Example 2

Context Dependent Choice of Relevant Protocols or Parts

A particular protocol "A" was used by two different users, who then subsequently scored the protocol and recorded the value of a series of process factors for each instance of use of the protocol (table 1).

TABLE 1

Sample score table for protocol A

| Temperature | Glycerol Content | Incubation Speed | Score | User | Object |
|---|---|---|---|---|---|
| 20 | 50 | 1200 | 5 | 1 | A |
| 25 | 25 | 900 | 2 | 2 | A |
| 37 | 75 | 1500 | 1 | 1 | A |

FIG. 3 shows an example score presentation window obtained for a specific context, based on the data stored in table 1. A user specified the process factors associated with the intended use of protocol A. This information was used by the method to extract the scores that are most relevant to the user in this particular context, and display the score of protocol A in this context. A confidence of 1 was also displayed, reflecting the fact that the particular contextual score displayed is based on a single instance of use by a single user.

Unless otherwise indicated, the practice of the present invention employs conventional techniques of chemistry, computer science, statistics, molecular biology, microbiology, recombinant DNA technology, and chemical methods, which are within the capabilities of a person of ordinary skill in the art. Such techniques are also explained in the literature, for example, T. Cormen, C. Leiserson, R. Rivest, 2009, Introduction to Algorithms, $3^{rd}$ Edition, The MIT Press, Cambridge, Mass.; L. Eriksson, E. Johansson, N. Kettaneh-Wold, J. Trygg, C. Wikstom, S. Wold, Multi- and Megavariate Data Analysis, Part 1, $2^{nd}$ Edition, 2006, UMetrics, UMetrics AB, Sweden; M. R. Green, J. Sambrook, 2012, Molecular Cloning: A Laboratory Manual, Fourth Edition, Books 1-3, Cold Spring Harbor Laboratory Press, Cold Spring Harbor, N.Y.; Ausubel, F. M. et al. (1995 and periodic supplements; Current Protocols in Molecular Biology, ch. 9, 13, and 16, John Wiley & Sons, New York, N.Y.); B. Roe, J. Crabtree, and A. Kahn, 1996, DNA Isolation and Sequencing: Essential Techniques, John Wiley & Sons; J. M. Polak and James O'D. McGee, 1990, In Situ Hybridisation: Principles and Practice, Oxford University Press; M. J. Gait (Editor), 1984, Oligonucleotide Synthesis: A Practical Approach, IRL Press; and D. M. J. Lilley and J. E. Dahlberg, 1992, Methods of Enzymology: DNA Structure Part A: Synthesis and Physical Analysis of DNA Methods in Enzymology, Academic Press. Each of these general texts is herein incorporated by reference.

Although particular embodiments of the invention have been disclosed herein in detail, this has been done by way of example and for the purposes of illustration only. The aforementioned embodiments are not intended to be limiting with respect to the scope of the appended claims, which follow. It is contemplated by the inventors that various substitutions, alterations, and modifications may be made to the invention without departing from the spirit and scope of the invention as defined by the claims.

What is claimed is:

1. A method for scoring a unit operation comprised within a biological process undertaken by a user, the method comprising:
    (a) recording input received from a user including a score associated with an instance of use of a unit operation within a database, wherein the unit operation is one of a plurality of self-contained processes including at least one physical element that collectively constitute a biological process for producing a physical output and a context of a use of the unit operation is recorded along with the score, and wherein the context is indicative of situational information uniquely associated with the user and the context of the use of the unit operation includes a value of at least one factor that is deemed to affect the performance of the unit operation within the biological process;
    (b) receiving a query from the user, the query specifying a proposed unit operation and a proposed context for an intended use of the proposed unit operation; and
    (c) returning a recorded score retrieved from the database for a relevant recorded unit operation, in response to the query, wherein relevance of the recorded score is determined at least partially based on a similarity defined by a distance between the context of the intended use of the proposed unit operation and the context of the recorded instance of use of the relevant recorded unit operation in a multidimensional context space.

2. The method of claim 1, wherein a score comprises one or more user-defined ratings.

3. The method of claim 1, wherein a score comprises one or more measurable features associated with the use of the part or protocol.

4. The method of claim 1, comprising, prior to returning the recorded score retrieved from the database:
    prompting the user to specify the value of specific factors.

5. The method of claim 1, wherein the user specifies criteria on scores to be included or excluded.

6. The method of claim 5, wherein recorded scores within a user-defined distance from the proposed context are returned.

7. The method of claim 5, wherein scores within a user-specified area of the context space are returned.

8. The method of claim 1, further comprising:
    returning a set maximum number of alternative parts or protocols in response to the query.

9. The method of claim 1, wherein a score is associated with a confidence metric.

10. The method of claim 9, wherein the confidence is defined in relation to the user who defined the score.

11. The method of claim 10, wherein the confidence is calculated based on how many scores were submitted by a user, and how often a user's scores agrees with other users.

12. The method of claim 9, wherein the confidence is defined in relation to an amount of contextual information provided with the score.

13. The method of claim 1, wherein the distance is a Euclidian distance.

14. The method of claim 1, wherein cut-offs for scores to be considered are dynamically defined based on a statistical metric of reliability.

15. The method of claim 1, wherein context of a part, protocol or unit operation comprises features of preceding or subsequent unit operations.

16. The method of claim 15, wherein incompatible options are automatically filtered.

17. The method of claim 1, wherein the user may prioritize features of interest in an evaluation of the similarity between contexts.

18. The method of claim 17, further comprising:
    specifying weights or rank of features of contexts to be compared.

19. The method of claim 1, wherein multivariate models may be fitted to describe the scoring space.

20. One or more non-transitory computer readable mediums storing a database and instructions which, when executed by a processor, cause the processor to:

store a plurality of unit operations in the database, each unit operation being suitable for use within a plurality of biological processes and the plurality of unit operations that collectively constitute a biological process for producing a physical output, wherein each unit operation is defined as a self-contained process included in a protocol that requires the use of at least one physical part in order to complete the protocol;

store a plurality of multidimensional scores in the database, each multidimensional score being defined in a multidimensional space and associated with a respective unit operation; and return a stored multidimensional score retrieved from the database in response to a query specifying a proposed unit operation, the returned multidimensional score associated with a relevant stored unit operation determined at least partially based on a similarity defined as a distance between the returned multidimensional score of the proposed unit operation and a multidimensional score of the relevant stored unit operation.

21. The computer readable medium of claim 20, wherein the multidimensional score comprises at least one user-defined rating.

22. The computer readable medium of claim 21, wherein a multidimensional score further comprises at least one item of contextual information, wherein the at least one item of contextual information comprises the value of at least one factor that is deemed to affect the performance of a unit operation within the biological process.

23. An apparatus comprising the non-transitory computer readable medium and the processor of claim 20.

* * * * *